United States Patent [19]

Westphalen

[11] Patent Number: 5,143,538
[45] Date of Patent: * Sep. 1, 1992

[54] N-((6-TRIFLUOROMETHYLPYRIMIDIN-2-YL)-AMINOCARBONYL)-2-CARBOALKOXYBENZENESULFONAMIDES, AND THEIR USE

[76] Inventor: Karl-Otto Westphalen, 58 Mausbergweg, 6720 Speyer, Fed. Rep. of Germany

[*] Notice: The portion of the term of this patent subsequent to Dec. 3, 2008 has been disclaimed.

[21] Appl. No.: 704,235

[22] Filed: May 22, 1991

Related U.S. Application Data

[62] Division of Ser. No. 337,866, Apr. 14, 1989, Pat. No. 5,069,710.

[30] Foreign Application Priority Data

Apr. 22, 1988 [DE] Fed. Rep. of Germany ....... 3813623

[51] Int. Cl.$^5$ .................. C07D 239/69; C07D 239/47; A01N 43/54
[52] U.S. Cl. ........................................ 71/92; 544/332; 544/321
[58] Field of Search ...................... 71/92; 544/321, 332

[56] References Cited

U.S. PATENT DOCUMENTS

| 4,169,719 | 10/1979 | Levitt | 71/92 |
| 4,383,113 | 5/1983 | Levitt | 544/211 |
| 4,592,978 | 12/1983 | Levitt | 544/321 |
| 4,661,147 | 4/1987 | Dumas | 71/92 |

Primary Examiner—John M. Ford
Attorney, Agent, or Firm—Keil & Weinkauf

[57] ABSTRACT

N-((6-Trifluoromethylpyrimidin-2-yl)-aminocarbonyl)-2-carboalkoxybenzenesulfonamides of the general formula Ia where the substitutents have the following meanings:
$R^1$ is hydrogen or halogen;
$R^2$ is hydrogen, $C_1$–$C_5$-alkyl, $C_3$–$C_4$-alkenyl, $C_3$–$C_4$-alkynyl, $C_1$–$C_5$-haloalkyl, $C_3$–$C_5$-alkoxyalkyl, $C_3$–$C_5$-haloalkoxyalkyl or $C_5$–$C_6$-cycloalkyl,
$R^3$ is hydrogen, $C_1$–$C_2$-alkyl, allyl, propargyl or $C_1$–$C_5$-alkoxy,
$R^4$ is halogen, $C_1$–$C_2$-alkyl, $C_1$–$C_3$-alkylamino,
$R^3$ not denoting hydrogen or $C_1$–$C_2$-alkyl when $R^4$ is $C_1$–2-alkyl, and their environmentally tolerated salts, processes for their manufacture, and their use.

12 Claims, No Drawings

N-((6-TRIFLUOROMETHYLPYRIMIDIN-2-YL)-AMINOCARBONYL)-2-CARBOALKOXYBEN-ZENESULFONAMIDES, AND THEIR USE

This is a divisional of application Ser. No. 07/337,866, filed Apr. 14, 1989, now U.S. Pat. No. 5,069,710.

The present invention relates to N-((6-trifluoromethylpyrimidin-2-yl)-aminocarbonyl)-2-carboalkoxybenzenesulfonamides of the general formula Ia

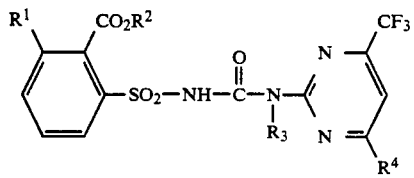

where $R^1$ is hydrogen or halogen, $R^2$ is hydrogen, $C_1$-$C_5$-alkyl, $C_3$- or $C_4$-alkenyl, $C_3$- or $C_4$-alkynyl, $C_1$-$C_5$-haloalkyl, $C_3$-$C_5$-alkoxyalkyl, $C_3$-$C_5$-haloalkoxyalkyl or $C_5$- or $C_6$-cycloalkyl, $R^3$ is hydrogen, $C_1$- or $C_2$-alkyl, allyl, propargyl or $C_1$-$C_5$-alkoxy and $R^4$ is halogen, $C_1$- or $C_2$-alkyl, $C_1$-$C_3$-alkylthio or $C_1$-$C_3$-alkylamino, and $R^3$ is not hydrogen or $C_1$- or $C_2$-alkyl when $R^4$ is $C_1$- or $C_2$-alkyl, and their environmentally compatible salts, and N-((6-trifluoromethylpyrimidin-2-yl)-aminocarbonyl)-2-carboalkoxybenzenesulfonamides of the general formula Ib

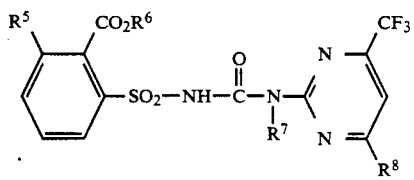

where $R^5$ is hydrogen, fluorine or chlorine, $R^6$ is $C_1$-$C_3$-alkyl, $R^7$ is hydrogen or methyl and $R^8$ is hydrogen or $C_1$- or $C_2$-alkoxy.

The present invention relates in particular to N-((6-trifluoromethylpyrimidin-2-yl)-aminocarbonyl)-2-carboalkoxybenzenesulfonamides of the general formulae Ia and Ib in which $R^2$ and $R^6$, respectively, are methyl, and those in which $R^4$ and $R^8$, respectively, are chlorine, methoxy or methylthio.

The present invention furthermore relates to processes for the preparation of the compounds Ia and Ib and herbicides which contain these compounds.

U.S. Pat. No. 4,169,719 discloses sulfonylureas having a herbicidal action. Furthermore, EP-A 7687 describes herbicidal sulfonylureas whose general formula embraces the N-((6-trifluoromethylpyrimidin-2-yl)-aminocarbonyl)-2-carboalkoxybenzenesulfonamides of the general formula Ib, defined at the outset. However, the known agents do not meet all requirements with respect to specific activity against undesirable plants and toleration by crops.

It is an object of the present invention to find and synthesize sulfonylureas which have advantageous properties compared with the known active ingredients of this class of herbicides.

We have found that this object is achieved by the N-((6-trifluoromethylpyrimidinyl-2-yl)-aminocarbonyl)-2-carboalkoxybenzenesulfonamides of the general formulae Ia and Ib, defined at the outset.

A sulfonylurea of the formula Ia or Ib is obtained, for example, by reacting a corresponding compound of the formula IIa or IIb, respectively,

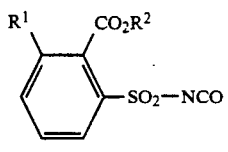 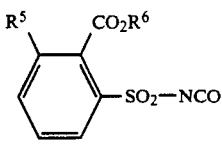

IIa  IIb with a corresponding compound of the formula IIIa or IIIb, respectively,

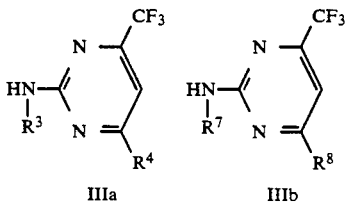

IIIa  IIIb at a temperature of up to 120° C., preferably from 10° to 100° C., which is conventionally used for organic reactions. The reaction can be carried out under atmospheric or superatmospheric pressure, continuously or batchwise.

The sulfonylureas of the formulae Ia and Ib can also be obtained by reacting a corresponding sulfonamide of the formula IVa or IVb, respectively,

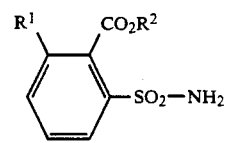 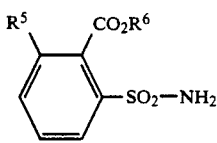

IVa  IVb with a corresponding phenyl carbamate of the formula Va or Vb, respectively,

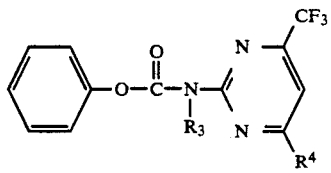

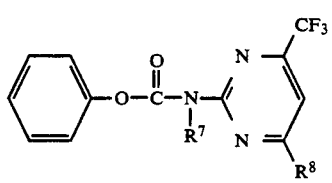

advantageously in the presence of a tertiary amine at a temperature of up to 120° C., preferably from 10° to 100° C., which is conventionally used for organic reactions.

The sulfonylureas of the formulae Ia and Ib may furthermore be obtained by reacting a corresponding phenyl carbamate of the formula VIa or VIb, respectively,

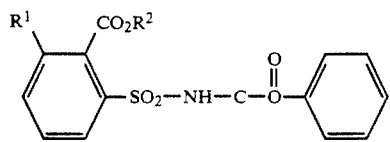

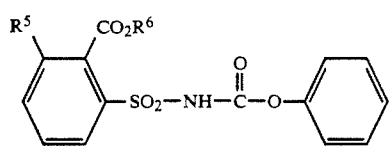

with a corresponding amine of the formula IIIa or IIIb, respectively,

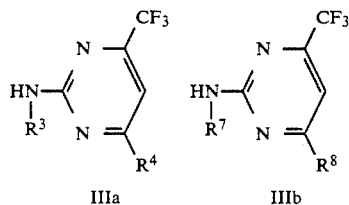

advantageously in the presence of a tertiary amine at a temperature of up to 120° C., preferably from 10° to 100° C., which is conventionally used for organic reactions.

Solvents or diluents are advantageously used for the reactions. Examples of suitable solvents are halohydrocarbons, in particular chlorohydrocarbons, e.g. tetrachloroethylene, 1,1,2,2- and 1,1,1,2-tetrachloroethane, dichloropropane, methylene chloride, dichlorobutane, chloroform, chloronaphthalene, dichloronaphthalene, carbon tetrachloride, 1,1,1- and 1,1,2-trichloroethane, trichloroethylene, pentachloroethane, o-, m- and p-difluorobenzene, 1,2-dichloroethane, 1,1-dichloroethane, 1,2-cis-dichloroethylene, chlorobenzene, fluorobenzene, bromobenzene, iodobenzene, o-, m- and p-dichlorobenzene, o-, p- and m-dibromobenzene, o-, m- and p-chlorotoluene and 1,2,4-trichlorobenzene; ethers, e.g. ethyl propyl ether, methyl tert.-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane, thioanisole and $\beta,\beta'$-dichlorodiethyl ether; nitrohydrocarbons, such as o-, m- and p-chloronitrobenzene and o-nitrotoluene; nitriles, such as acetonitrile, butyronitrile, isobutyronitrile, benzonitrile and m-chlorobenzonitrile; aliphatic and cycloaliphatic hydrocarbons, e.g. heptane, pinane, nonane, o-, m- and p-cymene, gasoline fractions boiling within a range of from 70° to 190° C., cyclohexane, methylcyclohexane, decalin, petroleum ether, hexane, naphtha, 2,2,4-trimethylpentane, 2,2,3-trimethylpentane and octane; esters, e.g. ethyl acetate, ethyl acetoacetate and isobutyl acetate; amides, e.g. formamide, methylformamide and dimethylformamide; ketones, e.g. acetone and methyl ethyl ketone, and mixtures of these. The solvent is advantageously used in an amount of from 100 to 2000, preferably from 200 to 700, % by weight, based on the starting materials II, IV or VI.

The compounds III or V required for the reaction are generally used in a roughly stoichiometric ratio. The intermediates II, IV or VI may be initially taken in a diluent and the intermediate III or V then added.

However, the process for the preparation of the novel compounds is advantageously carried out by initially taking the intermediate III or V and adding the intermediate II or IV or VI.

The reactions are generally complete in the course of from 20 minutes to 24 hours at from 0° to 120° C., preferably from 10° to 100° C., in particular from 20° to 80° C.

In the reactions which can be advantageously affected by the presence of a tertiary amine as a reaction accelerator, for example pyridine, 2,4- or 2,6-lutidine, 2,4,6-collidine, $\alpha,\beta$-picoline, p-dimethylaminopyridine, 1,4-diaza[2.2.2]bicyclooctane (DABCO) or 1,8-diazabicyclo[5.4.0]undec-7-ene are used, in an amount of not more than 1 mole per mole of intermediate IV or VI.

If the sulfonylureas are in the form of an acid, the salt can be prepared by reaction with a stoichiometric amount of an aqueous base or of a metal alcoholate, in the presence or absence of an organic solvent. Another possibility is alkaline hydrolysis of the corresponding esters.

The end products are obtained from the particular reaction mixtures in a conventional manner, for example after distilling off solvents or directly by filtration under suction. The remaining residue can furthermore be washed with water or a dilute acid to remove basic impurities. However, it is also possible for the residue to be dissolved in a water-miscible solvent and the solution washed in the manner described. The desired end products are obtained in this case in pure form; if necessary, they can be purified by recrystallization or chromatography.

The compounds of the formulae II, III, IV, V and VI which are required as intermediates can be prepared by reactions known from the literature. For example, the preparation of the starting materials III is described by Gershon (H. Gershon, A. T. Grefig and A. A. Scala, J. Heterocycl. Chem. 20 (1983) 219), or the starting materials can be prepared similarly to the methods described there.

With regard to the biological activity, preferred sulfonylureas of the formula Ia are those in which $R^1$ is hydrogen or halogen, such as fluorine, chlorine, bromine or iodine, in particular hydrogen, fluorine, chlorine or bromine, $R^2$ is hydrogen, alkyl, such as methyl, ethyl, propyl, 1-methylethyl, butyl, 1-methylpropyl, 2-methylpropyl or 1,1-dimethylethyl, in particular methyl, ethyl, propyl, 1-methylethyl or 1-methylpropyl, alkenyl, such as 1-propenyl, 2-propenyl, 1-butenyl, 2-butenyl or 3-butenyl, in particular 2-propenyl or 2-butenyl, alkynyl, such as 1-propynyl, 2-propynyl, 1-butynyl, 2-butynyl or 3-butynyl, in particular 2-propynyl or 2-butynyl, haloalkyl, such as fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl or pentafluoroethyl, in particular difluoromethyl, trifluoromethyl, 2,2,2-trifluoroethyl or pentafluoroethyl, alkoxyalkyl, such as 2-methoxyethyl, 2-methoxypropyl, 3-methoxypropyl, 2-methoxy-1-methylethyl, ethoxymethyl, 2-ethoxyethyl, 2-ethoxypropyl, 3-ethoxypropyl, 2-ethoxy-1-methylethyl or 1-ethoxy-1-methylethyl, in particular methoxyethyl or ethoxyethyl, haloalkoxyalkyl, such as difluoromethoxyethyl, trifluoromethoxyethyl, chlorodifluoromethoxyethyl, dichlorofluoromethoxyethyl, 1-fluoroethoxyethyl, 2-fluoroethoxyethyl, 2,2-difluoroethoxyethyl, 1,1,2,2-tetrafluoroethoxythyl, 2,2,2-trifluoroethoxyethyl, 2-chloro-1,1,2-trifluoroethoxyethyl or pentafluoroethoxyethyl, in particular trifluoromethoxyethyl, or cycloalkyl, such as cyclopentyl or cyclohexyl, $R^3$ is hydrogen, methyl, ethyl, allyl, propargyl or alkoxy, such as methoxy, ethoxy, propoxy, 1-methylethoxy, butoxy, 1-methylpropoxy, 2-methylpropoxy or 1,1-dimethylethoxy, in particular hydrogen, methyl, allyl, propargyl, methoxy or ethoxy, and $R^4$ is halogen as stated for $R^1$, in particular fluorine, chlorine or bromine, alkylthio, such as methylthio, ethylthio, propylthio or 1-methylethylthio, in particular methylthio, ethylthio or 1-methylethylthio, or alkylamino, such as methylamino, ethylamino, propylamino or 1-methylethylamino, in particular methylamino or ethylamino.

With regard to the biological activity, particularly preferred sulfonylureas of the formula Ib are those in which $R^5$ is hydrogen, fluorine or chlorine, $R^6$ is, in particular, methyl or ethyl, $R^7$ is hydrogen or methyl and $R^8$ is hydrogen, methoxy or ethoxy.

Regarding the biological activity, specific examples of herbicidal sulfonylureas of the general formula Ia are summarized in the table below.

TABLE

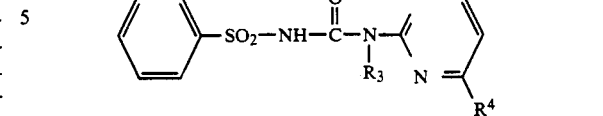

Ia

| $R^1$ | $R^2$ | $R^3$ | $R^4$ |
|---|---|---|---|
| H | CH₃ | H | Cl |
| H | C₂H₅ | H | Cl |
| H | n-C₃H₇ | H | Cl |
| H | n-C₄H₉ | H | Cl |
| H | i-C₃H₇ | H | Cl |
| H | sec-C₄H₉ | H | Cl |
| H | CH₂CH=CH₂ | H | Cl |
| H | CH₂C≡CH | H | Cl |
| H | CH₂CH₂Cl | H | Cl |
| H | CH₂CH₂OCH₃ | H | Cl |
| H | cyclohexyl | H | Cl |
| H | CH₃ | H | OCH₃ |
| H | C₂H₅ | H | OCH₃ |
| H | n-C₃H₇ | H | OCH₃ |
| H | n-C₄H₉ | H | OCH₃ |
| H | i-C₃H₇ | H | OCH₃ |
| H | sec-C₄H₉ | H | OCH₃ |
| H | CH₂CH=CH₂ | H | OCH₃ |
| H | CH₂C≡CH | H | OCH₃ |
| H | CH₂CH₂Cl | H | OCH₃ |
| H | CH₂CH₂OCH₃ | H | OCH₃ |
| H | cyclohexyl | H | OCH₃ |
| H | CH₃ | H | OC₂H₅ |
| H | C₂H₅ | H | OC₂H₅ |
| H | n-C₃H₇ | H | OC₂H₅ |
| H | n-C₄H₉ | H | OC₂H₅ |
| H | i-C₃H₇ | H | OC₂H₅ |
| H | sec-C₄H₉ | H | OC₂H₅ |
| H | CH₂CH=CH₂ | H | OC₂H₅ |
| H | CH₂C≡CH | H | OC₂H₅ |
| H | CH₂CH₂Cl | H | OC₂H₅ |
| H | CH₂CH₂OCH₃ | H | OC₂H₅ |
| H | cyclohexyl | H | OC₂H₅ |
| H | CH₃ | H | O-i-C₃H₇ |
| H | C₂H₅ | H | O-i-C₃H₇ |
| H | n-C₃H₇ | H | O-i-C₃H₇ |
| H | n-C₄H₉ | H | O-i-C₃H₇ |
| H | i-C₃H₇ | H | O-i-C₃H₇ |
| H | sec-C₄H₉ | H | O-i-C₃H₇ |
| H | CH₂CH=CH₂ | H | O-i-C₃H₇ |
| H | CH₂—C≡CH | H | O-i-C₃H₇ |
| H | CH₂CH₂Cl | H | O-i-C₃H₇ |
| H | CH₂CH₂OCH₃ | H | O-i-C₃H₇ |
| H | cyclohexyl | H | O-i-C₃H₇ |
| H | CH₃ | H | O-n-C₃H₇ |
| H | C₂H₅ | H | O-n-C₃H₇ |
| H | n-C₃H₇ | H | O-n-C₃H₇ |
| H | n-C₄H₉ | H | O-n-C₃H₇ |
| H | i-C₃H₇ | H | O-n-C₃H₇ |
| H | sec-C₄H₉ | H | O-n-C₃H₇ |
| H | CH₂CH=CH₂ | H | O-n-C₃H₇ |
| H | CH₂—C≡CH | H | O-n-C₃H₇ |
| H | CH₂CH₂Cl | H | O-n-C₃H₇ |
| H | CH₂CH₂OCH₃ | H | O-n-C₃H₇ |
| H | cyclohexyl | H | O-n-C₃H₇ |
| H | CH₃ | H | NHCH₃ |
| H | C₂H₅ | H | NHCH₃ |
| H | n-C₃H₇ | H | NHCH₃ |
| H | n-C₄H₉ | H | NHCH₃ |
| H | i-C₃H₇ | H | NHCH₃ |
| H | sec-C₄H₉ | H | NHCH₃ |
| H | CH₂CH=CH₂ | H | NHCH₃ |
| H | CH₂C≡CH | H | NHCH₃ |
| H | CH₂CH₂Cl | H | NHCH₃ |
| H | CH₂CH₂OCH₃ | H | NHCH₃ |
| H | cyclohexyl | H | NHCH₃ |
| H | CH₃ | H | SCH₃ |
| H | C₂H₅ | H | SCH₃ |
| H | n-C₃H₇ | H | SCH₃ |
| H | n-C₄H₉ | H | SCH₃ |
| H | i-C₃H₇ | H | SCH₃ |
| H | sec-C₄H₉ | H | SCH₃ |
| H | CH₂CH=CH₂ | H | SCH₃ |
| H | CH₂C≡CH | H | SCH₃ |
| H | CH₂CH₂Cl | H | SCH₃ |
| H | CH₂CH₂OCH₃ | H | SCH₃ |
| H | cyclohexyl | H | SCH₃ |
| H | CH₃ | H | SC₂H₅ |
| H | C₂H₅ | H | SC₂H₅ |
| H | n-C₃H₇ | H | SC₂H₅ |
| H | n-C₄H₉ | H | SC₂H₅ |
| H | i-C₃H₇ | H | SC₂H₅ |
| H | sec-C₄H₉ | H | SC₂H₅ |
| H | CH₂CH=CH₂ | H | SC₂H₅ |
| H | CH₂C≡CH | H | SC₂H₅ |
| H | CH₂CH₂Cl | H | SC₂H₅ |
| H | CH₂CH₂OCH₃ | H | SC₂H₅ |
| H | cyclohexyl | H | SC₂H₅ |
| H | n-C₃H₇ | H | SC₃H₇ |
| H | CH₃ | CH₃ | Cl |
| H | C₂H₅ | CH₃ | Cl |
| H | n-C₃H₇ | CH₃ | Cl |
| H | n-C₄H₉ | CH₃ | Cl |
| H | i-C₃H₇ | CH₃ | Cl |
| H | sec-C₄H₉ | CH₃ | Cl |
| H | CH₂CH=CH₂ | CH₃ | Cl |
| H | CH₂C≡CH | CH₃ | Cl |
| H | CH₂CH₂Cl | CH₃ | Cl |
| H | CH₂CH₂OCH₃ | CH₃ | Cl |
| H | cyclohexyl | CH₃ | Cl |
| H | CH₃ | CH₃ | OCH₃ |
| H | C₂H₅ | CH₃ | OCH₃ |
| H | n-C₃H₇ | CH₃ | OCH₃ |
| H | n-C₄H₉ | CH₃ | OCH₃ |
| H | i-C₃H₇ | CH₃ | OCH₃ |
| H | sec-C₄H₉ | CH₃ | OCH₃ |

TABLE-continued

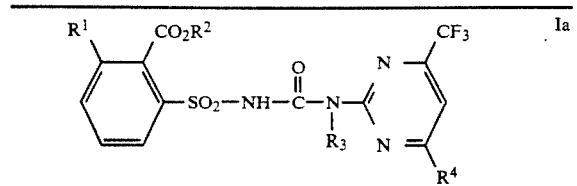

Ia

| $R^1$ | $R^2$ | $R^3$ | $R^4$ |
|---|---|---|---|
| H | CH$_2$CH=CH$_2$ | CH$_3$ | OCH$_3$ |
| H | CH$_2$C≡CH | CH$_3$ | OCH$_3$ |
| H | CH$_2$CH$_2$Cl | CH$_3$ | OCH$_3$ |
| H | CH$_2$CH$_2$OCH$_3$ | CH$_3$ | OCH$_3$ |
| H | cyclohexyl | CH$_3$ | OCH$_3$ |
| H | CH$_3$ | CH$_3$ | NHCH$_3$ |
| H | C$_2$H$_5$ | CH$_3$ | NHCH$_3$ |
| H | n-C$_3$H$_7$ | CH$_3$ | NHCH$_3$ |
| H | n-C$_4$H$_9$ | CH$_3$ | NHCH$_3$ |
| H | i-C$_3$H$_7$ | CH$_3$ | NHCH$_3$ |
| H | sec-C$_4$H$_9$ | CH$_3$ | NHCH$_3$ |
| H | CH$_2$CH=CH$_2$ | CH$_3$ | NHCH$_3$ |
| H | CH$_2$C≡CH | CH$_3$ | NHCH$_3$ |
| H | CH$_2$CH$_2$Cl | CH$_3$ | NHCH$_3$ |
| H | CH$_2$CH$_2$OCH$_3$ | CH$_3$ | NHCH$_3$ |
| H | cyclohexyl | CH$_3$ | NHCH$_3$ |
| H | CH$_3$ | OCH$_3$ | Cl |
| H | C$_2$H$_5$ | OCH$_3$ | Cl |
| H | n-C$_3$H$_7$ | OCH$_3$ | Cl |
| H | n-C$_4$H$_9$ | OCH$_3$ | Cl |
| H | i-C$_3$H$_7$ | OCH$_3$ | Cl |
| H | sec-C$_4$H$_9$ | OCH$_3$ | Cl |
| H | CH$_2$CH=CH$_2$ | OCH$_3$ | Cl |
| H | CH$_2$C≡CH | OCH$_3$ | Cl |
| H | CH$_2$CH$_2$Cl | OCH$_3$ | Cl |
| H | CH$_2$CH$_2$OCH$_3$ | OCH$_3$ | Cl |
| H | cyclohexyl | OCH$_3$ | Cl |
| H | CH$_3$ | OCH$_3$ | OCH$_3$ |
| H | C$_2$H$_5$ | OCH$_3$ | OCH$_3$ |
| H | n-C$_3$H$_7$ | OCH$_3$ | OCH$_3$ |
| H | n-C$_4$H$_9$ | OCH$_3$ | OCH$_3$ |
| H | i-C$_3$H$_7$ | OCH$_3$ | OCH$_3$ |
| H | sec-C$_4$H$_9$ | OCH$_3$ | OCH$_3$ |
| H | CH$_2$CH=CH$_2$ | OCH$_3$ | OCH$_3$ |
| H | CH$_2$C≡CH | OCH$_3$ | OCH$_3$ |
| H | CH$_2$CH$_2$Cl | OCH$_3$ | OCH$_3$ |
| H | CH$_2$CH$_2$OCH$_3$ | OCH$_3$ | OCH$_3$ |
| H | cyclohexyl | OCH$_3$ | OCH$_3$ |
| H | CH$_3$ | OCH$_3$ | CH$_3$ |
| H | C$_2$H$_5$ | OCH$_3$ | CH$_3$ |
| H | n-C$_3$H$_7$ | OCH$_3$ | CH$_3$ |
| H | n-C$_4$H$_9$ | OCH$_3$ | CH$_3$ |
| H | i-C$_3$H$_7$ | OCH$_3$ | CH$_3$ |
| H | sec-C$_4$H$_9$ | OCH$_3$ | CH$_3$ |
| H | CH$_2$CH=CH$_2$ | OCH$_3$ | CH$_3$ |
| H | CH$_2$C≡CH | OCH$_3$ | CH$_3$ |
| H | CH$_2$CH$_2$Cl | OCH$_3$ | CH$_3$ |
| H | CH$_2$CH$_2$OCH$_3$ | OCH$_3$ | CH$_3$ |
| H | cyclohexyl | OCH$_3$ | CH$_3$ |
| H | CH$_3$ | OCH$_3$ | NHCH$_3$ |
| H | C$_2$H$_5$ | OCH$_3$ | NHCH$_3$ |
| H | n-C$_3$H$_7$ | OCH$_3$ | NHCH$_3$ |
| H | n-C$_4$H$_9$ | OCH$_3$ | NHCH$_3$ |
| H | i-C$_3$H$_7$ | OCH$_3$ | NHCH$_3$ |
| H | sec-C$_4$H$_9$ | OCH$_3$ | NHCH$_3$ |
| H | CH$_2$CH=CH$_2$ | OCH$_3$ | NHCH$_3$ |
| H | CH$_2$C≡CH | OCH$_3$ | NHCH$_3$ |
| H | CH$_2$CH$_2$Cl | OCH$_3$ | NHCH$_3$ |
| H | CH$_2$CH$_2$OCH$_3$ | OCH$_3$ | NHCH$_3$ |
| H | cyclohexyl | OCH$_3$ | NHCH$_3$ |
| H | CH$_3$ | CH$_2$CH=CH$_2$ | Cl |
| H | C$_2$H$_5$ | CH$_2$CH=CH$^2$ | Cl |
| H | n-C$_3$H$_7$ | CH$_2$CH=CH$_2$ | Cl |
| H | n-C$_4$H$_9$ | CH$_2$CH=CH$_2$ | Cl |
| H | i-C$_3$H$_7$ | CH$_2$CH=CH$_2$ | Cl |
| H | sec-C$_4$H$_9$ | CH$_2$CH=CH$_2$ | Cl |
| H | CH$_2$CH=CH$_2$ | CH$_2$CH=CH$_2$ | Cl |
| H | CH$_2$C≡CH | CH$_2$CH=CH$_2$ | Cl |
| H | CH$_2$CH$_2$Cl | CH$_2$CH=CH$_2$ | Cl |
| H | CH$_2$CH$_2$OCH$_3$ | CH$_2$CH=CH$_2$ | Cl |
| H | cyclohexyl | CH$_2$CH=CH$_2$ | Cl |

TABLE-continued

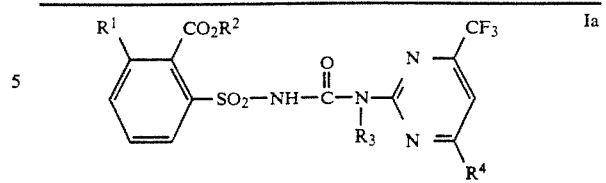

Ia

| $R^1$ | $R^2$ | $R^3$ | $R^4$ |
|---|---|---|---|
| H | CH$_3$ | CH$_2$CH=CH$_2$ | OCH$_3$ |
| H | C$_2$H$_5$ | CH$_2$CH=CH$_2$ | OCH$_3$ |
| H | n-C$_3$H$_7$ | CH$_2$CH=CH$_2$ | OCH$_3$ |
| H | n-C$_4$H$_9$ | CH$_2$CH=CH$_2$ | OCH$_3$ |
| H | i-C$_3$H$_7$ | CH$_2$CH=CH$_2$ | OCH$_3$ |
| H | sec-C$_4$H$_9$ | CH$_2$CH=CH$_2$ | OCH$_3$ |
| H | CH$_2$CH=CH$_2$ | CH$_2$CH=CH$_2$ | OCH$_3$ |
| H | CH$_2$C≡CH | CH$_2$CH=CH$_2$ | OCH$_3$ |
| H | CH$_2$CH$_2$Cl | CH$_2$CH=CH$_2$ | OCH$_3$ |
| H | CH$_2$CH$_2$OCH$_3$ | CH$_2$CH=CH$_2$ | OCH$_3$ |
| H | cyclohexyl | CH$_2$CH=CH$_2$ | OCH$_3$ |
| H | CH$_3$ | CH$_2$CH=CH$_2$ | CH$_3$ |
| H | C$_2$H$_5$ | CH$_2$CH=CH$_2$ | CH$_3$ |
| H | n-C$_3$H$_7$ | CH$_2$CH=CH$_2$ | CH$_3$ |
| H | n-C$_4$H$_9$ | CH$_2$CH=CH$_2$ | CH$_3$ |
| H | i-C$_3$H$_7$ | OCH$_3$ | CH$_3$ |
| H | sec-C$_4$H$_9$ | OCH$_3$ | CH$_3$ |
| H | CH$_2$CH=CH$_2$ | OCH$_2$ | CH$_3$ |
| H | CH$_2$C≡CH | OCH$_3$ | CH$_3$ |
| H | CH$_2$CH$_2$Cl | OCH$_3$ | CH$_3$ |
| H | CH$_2$CH$_2$OCH$_3$ | OCH$_3$ | CH$_3$ |
| H | cyclohexyl | OCH$_3$ | CH$_3$ |
| H | CH$_3$ | CH$_2$CH=CH$_2$ | NHCH$_3$ |
| H | C$_2$H$_5$ | CH$_2$CH=CH$_2$ | NHCH$_3$ |
| H | n-C$_3$H$_7$ | CH$_2$CH=CH$_2$ | NHCH$_3$ |
| H | n-C$_4$H$_9$ | CH$_2$CH=CH$_2$ | NHCH$_3$ |
| H | i-C$_3$H$_7$ | CH$_2$CH=CH$_2$ | NHCH$_3$ |
| H | sec-C$_4$H$_9$ | CH$_2$CH=CH$_2$ | NHCH$_3$ |
| H | CH$_2$CH=CH$_2$ | CH$_2$CH=CH$_2$ | NHCH$_3$ |
| H | CH$_2$C≡CH | CH$_2$CH=CH$_2$ | NHCH$_3$ |
| H | CH$_2$CH$_2$Cl | CH$_2$CH=CH$_2$ | NHCH$_3$ |
| H | CH$_2$CH$_2$OCH$_3$ | CH$_2$CH=CH$_2$ | NHCH$_3$ |
| H | cyclohexyl | CH$_2$CH=CH$_2$ | NHCH$_3$ |
| Cl | CH$_3$ | H | Cl |
| Cl | C$_2$H$_5$ | H | Cl |
| Cl | n-C$_3$H$_7$ | H | Cl |
| Cl | n-C$_6$H$_9$ | H | Cl |
| Cl | i-C$_3$H$_7$ | H | Cl |
| Cl | sec-C$_4$H$_9$ | H | Cl |
| Cl | CH$_2$CH=CH$_2$ | H | Cl |
| Cl | CH$_2$C≡CH | H | Cl |
| Cl | CH$_2$CH$_2$Cl | H | Cl |
| Cl | CH$_2$CH$_2$OCH$_3$ | H | Cl |
| Cl | cyclohexyl | H | Cl |
| Cl | CH$_3$ | H | OCH$_3$ |
| Cl | C$_2$H$_5$ | H | OCH$_3$ |
| Cl | n-C$_3$H$_7$ | H | OCH$_3$ |
| Cl | n-C$_4$H$_9$ | H | OCH$_3$ |
| Cl | i-C$_3$H$_7$ | H | OCH$_3$ |
| Cl | sec-C$_4$H$_9$ | H | OCH$_3$ |
| Cl | CH$_2$CH=CH$_2$ | H | OCH$_3$ |
| Cl | CH$_2$C≡CH | H | OCH$_3$ |
| Cl | CH$_2$CH$_2$Cl | H | OCH$_3$ |
| Cl | CH$_2$CH$_2$OCH$_3$ | H | OCH$_3$ |
| Cl | cyclohexyl | H | OCH$_3$ |
| Cl | CH$_3$ | CH$_3$ | Cl |
| Cl | C$_2$H$_5$ | CH$_3$ | Cl |
| Cl | n-C$_3$H$_7$ | CH$_3$ | Cl |
| Cl | n-C$_4$H$_9$ | CH$_3$ | Cl |
| Cl | i-C$_3$H$_7$ | CH$_3$ | Cl |
| Cl | sec-C$_4$H$_9$ | CH$_3$ | Cl |
| Cl | CH$_2$CH=CH$_2$ | CH$_3$ | Cl |
| Cl | CH$_2$C≡CH | CH$_3$ | Cl |
| Cl | CH$_2$CH$_2$Cl | CH$_3$ | Cl |
| Cl | CH$_2$CH$_2$OCH$_3$ | CH$_3$ | Cl |
| Cl | cyclohexyl | CH$_3$ | Cl |
| Cl | CH$_3$ | CH$_3$ | OCH$_3$ |
| Cl | C$_2$H$_5$ | CH$_3$ | OCH$_3$ |
| Cl | n-C$_3$H$_7$ | CH$_3$ | OCH$_3$ |
| Cl | n-C$_4$H$_9$ | CH$_3$ | OCH$_3$ |
| Cl | i-C$_3$H$_7$ | CH$_3$ | OCH$_3$ |

TABLE-continued

Ia $$R^1\text{-}C_6H_3(CO_2R^2)\text{-}SO_2\text{-}NH\text{-}C(=O)\text{-}N(R_3)\text{-}\text{pyrimidine}(CF_3)(R^4)$$

| R¹ | R² | R³ | R⁴ |
|---|---|---|---|
| Cl | sec-C₄H₉ | CH₃ | OCH₃ |
| Cl | CH₂CH=CH₂ | CH₃ | OCH₃ |
| Cl | CH₂C≡CH | CH₃ | OCH₃ |
| Cl | CH₂CH₂Cl | CH₃ | OCH₃ |
| Cl | CH₂CH₂OCH₃ | CH₃ | OCH₃ |
| Cl | cyclohexyl | CH₃ | OCH₃ |
| F | CH₃ | H | Cl |
| F | C₂H₅ | H | Cl |
| F | n-C₃H₇ | H | Cl |
| F | n-C₄H₉ | H | Cl |
| F | i-C₃H₇ | H | Cl |
| F | sec-C₄H₉ | H | Cl |
| F | CH₂CH=CH₂ | H | Cl |
| F | CH₂C≡CH | H | Cl |
| F | CH₂CH₂Cl | H | Cl |
| F | CH₂CH₂OCH₃ | H | Cl |
| F | cyclohexyl | H | Cl |
| F | CH₃ | H | OCH₃ |
| F | C₂H₅ | H | OCH₃ |
| F | n-C₃H₇ | H | OCH₃ |
| F | n-C₄H₉ | H | OCH₃ |
| F | i-C₃H₇ | H | OCH₃ |
| F | sec-C₄H₉ | H | OCH₃ |
| F | CH₂CH=CH₂ | H | OCH₃ |
| F | CH₂C≡CH | H | OCH₃ |
| F | CH₂CH₂Cl | H | OCH₃ |
| F | CH₂CH₂OCH₃ | H | OCH₃ |
| F | cyclohexyl | H | OCH₃ |
| F | CH₃ | H | SCH₃ |
| F | CH₃ | CH₃ | Cl |
| F | C₂H₅ | CH₃ | Cl |
| F | n-C₃H₇ | CH₃ | Cl |
| F | n-C₄H₉ | CH₃ | Cl |
| F | i-C₃H₇ | CH₃ | Cl |
| F | sec-C₄H₉ | CH₃ | Cl |
| F | CH₂CH=CH₂ | CH₃ | Cl |
| F | CH₂C≡CH | CH₃ | Cl |
| F | CH₂CH₂Cl | CH₃ | Cl |
| F | CH₂CH₂OCH₃ | CH₃ | Cl |
| F | cyclohexyl | CH₃ | Cl |
| F | CH₃ | CH₃ | OCH₃ |
| F | C₂H₅ | CH₃ | OCH₃ |
| F | n-C₃H₇ | CH₃ | OCH₃ |
| F | n-C₄H₉ | CH₃ | OCH₃ |
| F | i-C₃H₇ | CH₃ | OCH₃ |
| F | sec-C₄H₉ | CH₃ | OCH₃ |
| F | CH₂CH=CH₂ | CH₃ | OCH₃ |
| F | CH₂C≡CH | CH₃ | OCH₃ |
| F | CH₂CH₂Cl | CH₃ | OCH₃ |
| F | CH₂CH₂OCH₃ | CH₃ | OCH₃ |
| F | cyclohexyl | CH₃ | OCH₃ |

The N-((6-trifluoromethylpyrimidin-2-yl)-aminocarbonyl)-2-carboalkoxybenzenesulfonamides of the general formulae Ia and Ib, or herbicidal agents containing them, and the environmentally tolerated salts of alkali metals and alkaline earth metals, combat injurious plants excellently without damaging crop plants—an effect which is particularly apparent at low application rates. They may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

The compounds Ia and Ib are suitable for the preparation of solutions, emulsions, pastes and oil dispersions to be sprayed direct. Examples of inert additives are mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives, methanol, ethanol, propanol, butanol, chloroform, carbon tetrachloride, cyclohexanol, cyclohexanone, chlorobenzene, isophorone, etc., and strongly polar solvents such as N,N-dimethylformamide, dimethyl sulfoxide, N-methylpyrrolidone, water, etc.

Aqueous formulations may be prepared from emulsion concentrates, pastes, dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90% by weight of active ingredient.

The active ingredients may be formulated for instance as follows:

I. 90 parts by weight of compound no. 1.012 in mixed with 10 parts by weight of N-methyl-alpha-pyrrolidone. A mixture is obtained which is suitable for application in the form of very fine drops.

II. 20 parts by weight of compound no. 1.005 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 1.017 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 1.012 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 1.010 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 1.009 is intimately mixed with 97 parts by weight of particulate kaolin. A dust is obtained containing 3% by weight of the active ingredient.

VII. 30 parts by weight of compound no. 2.001 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 2.009 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients may be applied pre- or post-emergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.001 to 5.0, preferably 0.005 to 1.0, kg of active ingredient per hectare.

In view of the number of application methods possible, the compounds according to the invention, or agents containing them, may be used in a further large number of crops for removing unwanted plants. The following crops are given by way of example:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass |
| Daucus carota | carrots |
| Elais guineensis | oil palms |
| Fragaria vesca | strawberries |
| Glycine max | soybeans |
| Gossypium hirsutum (Gossypium arboreum, Gossypium herbaceum, Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicotiana tabacum (N. rustica) | tobacco |
| Olea europaea | olive trees |
| Oryza sativa | rice |
| Panicum miliaceum | millet |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |

| Botanical name | Common name |
| --- | --- |
| *Prunus avium* | cherry trees |
| *Prunus domestica* | plum trees |
| *Prunus dulcis* | almond trees |
| *Prunus persica* | peach trees |
| *Pyrus communis* | pear trees |
| *Ribes sylvestre* | redcurrants |
| *Ribes uva-crispa* | gooseberries |
| *Ricinus communis* | castor-oil plants |
| *Saccharum officinarum* | sugar cane |
| *Secale cereale* | rye |
| *Sesamum indicum* | sesame |
| *Solanum tuberosum* | Irish potatoes |
| *Sorghum bicolor (s. vulgare)* | sorghum |
| *Sorghum dochna* | sorgo |
| *Spinacia oleracea* | spinach |
| *Theobroma cacao* | cacao plants |
| *Trifolium pratense* | red clover |
| *Triticum aestivum* | wheat |
| *Triticum durum* | durum wheat |
| *Vaccinium corymbosum* | blueberries |
| *Vaccinium vitis-idaea* | cranberries |
| *Vicia faba* | tick beans |
| *Vigna sinensis (V. unguiculata)* | cow peas |
| *Vitis vinifera* | grapes |
| *Zea mays* | Indian corn, sweet corn, maize |

To increase the spectrum of action and to achieve synergistic effects, the sulfonylureas of the formula Ia and Ib may be mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, quinolinecarboxylic acids, phenyloxy- or heteroaryloxy-phenylpropionic acids and salts, esters and amides thereof, etc.

It may also be useful to apply the novel compounds of the formula Ia and Ib, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

SYNTHESIS EXAMPLE

Methyl 2-(((4-methoxy-6-trifluoromethyl-1,3-pyrimidin-2-yl)-aminocarbonyl)-aminosulfonyl)-benzoate At room temperature, 6.5 g of methyl 2-(isocyanatosulfonyl)-benzoate in 50 ml of absolute acetonitrile was introduced over a period of 10 minutes, with stirring and under a nitrogen blanket, to a suspension of 5.2 g of 2-amino-4-methoxy-6-trifluoromethyl-pyrimidine in 100 ml of absolute acetonitrile. The temperature rose by 10° C. After the reaction mixture had been stirred for 13 hours at 70° C., it was evaporated down and the residue was taken up in dichloromethane. The organic phase was washed once with 1N hydrochloric acid and once with 1N sodium hydroxide solution, dried with sodium sulfate and filtered. After the solvent had been stripped off, there was obtained 9.7 g of the title compound having a melting point of 150°–151° C.

The compounds given in the following tables were prepared by modifying the above example.

ACTIVE INGREDIENT TABLE 1

Ia

| Compound No. | $R^1$ | $R^2$ | $R^3$ | $R^4$ | mp(°) |
| --- | --- | --- | --- | --- | --- |
| 1.001 | H | $CH_3$ | H | Cl | 176–177 |
| 1.002 | H | $CH_3$ | H | $OCH(CH_3)_2$ | 170–173 |
| 1.003 | H | $CH_3$ | H | $NHCH_3$ | 115–117 |
| 1.004 | H | $CH_3$ | H | $SCH_3$ | 155–157 |
| 1.005 | H | $CH_3$ | H | $SCH_2CH_3$ | 71–73 |
| 1.006 | H | $CH_2CH_3$ | H | $SCH_3$ | 114–117 |
| 1.007 | H | $(CH_2)_2CH_3$ | H | $SCH_3$ | 146–148 |
| 1.008 | H | $(CH_2)_2CH_3$ | H | $S(CH_2)_2CH_3$ | 146–148 |
| 1.009 | F | $CH_3$ | H | Cl | 86–87 |
| 1.010 | F | $CH_3$ | H | $SCH_3$ | 181–187 |
| 1.011 | H | $CH_3$ | H | $S(CH_2)_2CH_3$ | 188–189 |
| 1.012 | Cl | $CH_3$ | H | $SCH_3$ | 204–206 |

ACTIVE INGREDIENT TABLE 2

Ib

| Compound No. | $R^5$ | $R^6$ | $R^7$ | $R^8$ | mp(°) |
| --- | --- | --- | --- | --- | --- |
| 2.001 | H | $CH_3$ | H | H | 160–168 |
| 2.002 | H | $CH_3$ | H | $OCH_3$ | 150–151 |
| 2.003 | H | $CH_3$ | H | $OCH_2CH_3$ | 150–152 |
| 2.004 | H | $CH_2CH_3$ | H | $OCH_3$ | 147–149 |
| 2.005 | H | $CH_2CH_3$ | H | $OCH_2CH_3$ | 130–132 |
| 2.006 | H | $(CH_2)_2CH_3$ | H | $OCH_3$ | 200–202 |
| 2.007 | H | $CH_3$ | $CH_3$ | $OCH_3$ | 137–139 |
| 2.008 | Cl | $CH_3$ | H | $OCH_3$ | 208–211 |
| 2.009 | F | $CH_3$ | H | $OCH_3$ | 179–182 |

The herbicidal action of the N-[(6-trifluoromethyl-pyrimidin-2-yl)-aminocarbonyl]-2-carboalkoxybenzenesulfonamides of the formulae Ia and Ib on plant growth is demonstrated by the following greenhouse experiments:

The vessels employed were plastic flowerpots having a volume of 300 cm$^3$ and filled with a sandy loam containing about 3.0% humus. The seeds of the test plants were sown separately, according to species.

For the preemergence treatment, the formulated active ingredients were applied to the surface of the soil immediately after the seeds had been sown. The compounds were emulsified or suspended in water as vehicle, and sprayed through finely distributing nozzles. The application rate was 0.03 kg of active ingredient per hectare. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were grown, depending on growth form, to a height of 3 to 15 cm before being treated. In this treatment method, either plants which had been sown in the pots and grown there were selected, or they were cultivated separately as seedlings and transplanted to the pots a few days before being treated. The application rates for postemergence treatment were 0.03 and 0.06 kg/ha. No covers were placed on the vessels in this method.

The pots were set up in the greenhouse, species from warmer climates in warmer areas (20° to 35° C.) and species from moderate climates at 10° to 20° C. The experiments were run for from 2 to 4 weeks. During this time the plants were tended and their reactions to the various treatments assessed. The assessment scale was 0 to 100, 100 denoting nonemergence or complete destruction of at least the visible plant parts, and 0 denoting no damage or normal growth.

The plants employed for the experiments were as follows:

| Abbrev. | Botanical name | Common name |
|---|---|---|
| ABUTH | Abutilon theophrasti | velvet leaf |
| AMARE | Amaranthus retroflexus | redroot pigweed |
| BROIN | Bromus inermis | smooth broome |
| CHEAL | Chenopodium album | lambsquarters (goosefoot) |
| CYPIR | Cyperus iria | flatsedge, rice |
| ECHCG | Echinochlora crus-galli | barnyardgrass |
| GALAP | Galium aparine | catchweed bedstraw |
| LAMAM | Lamium amplexicaule | henbit |
| POAAN | Poa annua | annual bluegrass |

| Abbrev. | Botanical name | Common name |
|---|---|---|
| VERSS | Veronica spp. | speedwell |

For comparison purposes, compounds from U.S. Pat. No. 4,169,719 having the structure A or B were employed and compared with the novel active ingredients in which $R^1$ has a carbalkoxy structure.

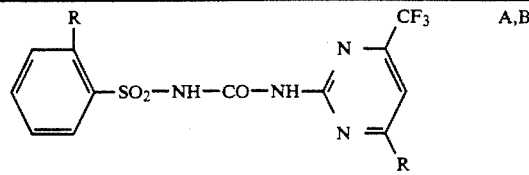

| Comp. agent | $R^1$ | $R^2$ | Ex. in U.S. Pat. No. 4,169,719 |
|---|---|---|---|
| A | Cl | $OCH_3$ | Tab. I-E |
| B | Cl | $CH_3$ | Tab. I-D |

Compounds 2.002 and 1.004, applied postemergence at rates of 0.03 and 0.06 kg/ha, had an excellent action on unwanted broadleaved plants, whereas A and B were virtually ineffective at these concentrations.

Compound 2.002, applied preemergence at a rate of 0.03 kg/ha, combated unwanted dicotyledonous and monocotyledonous plants very well; here again, A and B were virtually ineffective.

TABLE A

Control of unwanted broadleaved plants on postmergence application of 0.03 kg/ha in the greenhouse

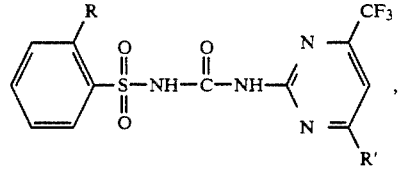

| Compound No. | R | R'(= $R^8$) | CYPIR | ECHCG | ABUTH | AMARE | GALAP | VERSS |
|---|---|---|---|---|---|---|---|---|
| 2.002 | $CO_2CH_3$ | $OCH_3$ | 100 | 98 | 98 | 100 | 100 | 100 |
| A* | Cl | $OCH_3$ | 0 | 0 | 0 | 0 | 0 | 0 |
| B** | Cl | $CH_3$ | 0 | 0 | 0 | 40 | 50 | 0 |

A* = from U.S. Pat. No. 4,169,719 (Tab. I-E)
B** = from U.S. Pat. No. 4,169,719 (Tab. I-D)

| STEME | Stellaria media | chickweed |
|---|---|---|

TABLE B

Control of unwanted broadleaved plants on preemergence application of 0.03 kg/ha in the greenhouse

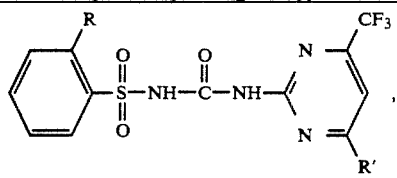

| Compound | R | R'(= $R^8$) | BROIN | ECHCG | POAAN | AMARE | CHEAL | GALAP | VERSS | CYPIR |
|---|---|---|---|---|---|---|---|---|---|---|
| 2.002 | $CO_2CH_3$ | $OCH_3$ | 98 | 98 | 98 | 98 | 98 | 95 | 100 | 100 |
| A* | Cl | $OCH_3$ | 0 | 0 | 0 | 0 | 0 | 0 | 0 | 0 |
| B** | Cl | $CH_3$ | 0 | 0 | 0 | 0 | 0 | 0 | 0 | 0 |

A* = from U.S. Pat. No. 4,169,719 (Tab. I-E)
B** = from U.S. Pat. No. 4,169,719 (Tab. I-D)

TABLE C

Control of unwanted broadleaved plants on postmergence application of 0.06 kg/ha of active ingredient no. 1.004 in the greenhouse

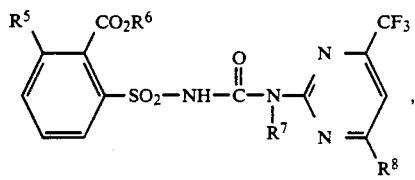

| Test plants | Damage in % |
|---|---|
| ABUTH | 100 |
| AMARE | 100 |
| CHEAL | 100 |
| LAMAM | 100 |
| STEME | 100 |

We claim:

1. An N-((6-Trifluoromethylpyrimidin-2-yl)-aminocarbonyl)-2-carboalkoxybenzenesulfonamide of the formula Ib where the substituents have the following meanings:
$R^5$ is hydrogen, fluorine or chlorine,
$R^6$ is $C_1$-$C_3$-alkyl,
$R^7$ is hydrogen or methyl, and
$R^8$ is hydrogen or $C_1$-$C_2$-alkoxy.

2. A compound as claimed in claim 1, where $R^6$ is methyl.

3. A compound as claimed in claim 1, wherein $R^8$ is methoxy.

4. A compound as claimed in claim 1, wherein $R^5$ is hydrogen, $R^6$ is methyl, $R^7$ is hydrogen, and $R^8$ is methoxy.

5. A herbicidal composition which comprises a herbicidally effective amount of a compound as claimed in claim 1, or an agriculturally useful salt thereof, and conventional auxiliaries or diluents.

6. A herbicidal composition which comprises a herbicidally effective amount of a compound as claimed in claim 2, or an agriculturally useful salt thereof, and conventional auxiliaries or diluents.

7. A herbicidal composition which comprises a herbicidally effective amount of a compound as claimed in claim 3, or an agriculturally useful salt thereof, and conventional auxiliaries or diluents.

8. A herbicidal composition which comprises a herbicidally effective amount of a compound as claimed in claim 4, or an agriculturally useful salt thereof, and conventional auxiliaries or diluents.

9. A process for combating unwanted plants, wherein a herbicidally effective amount of the compound claimed in claim 1, or an agriculturally useful salt thereof is applied to the plants and/or their habitat.

10. A process for combating unwanted plants, wherein a herbicidally effective amount of the compound claimed in claim 2, or an agriculturally useful salt thereof is applied to the plants and/or their habitat.

11. A process for combating unwanted plants, wherein a herbicidally effective amount of the compound claimed in claim 3, or an agriculturally useful salt thereof is applied to the plants and/or their habitat.

12. A process for combating unwanted plants, wherein a herbicidally effective amount of the compound claimed in claim 4, or an agriculturally useful salt thereof is applied to the plants and/or their habitat.

* * * * *

UNITED STATES PATENT AND TRADEMARK OFFICE
CERTIFICATE OF CORRECTION

PATENT NO. : 5,143,538

DATED : September 1, 1992

INVENTOR(S) : WESTPHALEN

It is certified that error appears in the above-identified patent and that said Letters Patent is hereby corrected as shown below:

In the Abstract, Line 11

After "$C_1$-$C_2$-alkyl" but before "$C_1$-$C_3$-alkylamino", please insert -- $C_1$-$C_3$-alkylthio --.

Signed and Sealed this

Fifth Day of October, 1993

Attest:

BRUCE LEHMAN

Attesting Officer

Commissioner of Patents and Trademarks